United States Patent
Minowa et al.

(10) Patent No.: US 8,076,503 B2
(45) Date of Patent: Dec. 13, 2011

(54) PROCESS FOR PRODUCTION OF OPTICALLY ACTIVE AMINOPHOSPHINYLBUTANOIC ACIDS

(75) Inventors: Nobuto Minowa, Yokohama (JP); Nozomu Nakanishi, Yokohama (JP); Masaaki Mitomi, Yokohama (JP); Hideki Nara, Hiratsuka (JP); Tohru Yokozawa, Hiratsuka (JP)

(73) Assignees: Meiji Seika Pharma Co., Ltd., Tokyo (JP); Takasago International Corporation, Tokyo (JP)

( * ) Notice: Subject to any disclaimer, the term of this patent is extended or adjusted under 35 U.S.C. 154(b) by 83 days.

(21) Appl. No.: 12/298,067

(22) PCT Filed: Sep. 3, 2007

(86) PCT No.: PCT/JP2007/067116
§ 371 (c)(1),
(2), (4) Date: Mar. 11, 2009

(87) PCT Pub. No.: WO2008/029754
PCT Pub. Date: Mar. 13, 2008

(65) Prior Publication Data
US 2009/0221851 A1    Sep. 3, 2009

(30) Foreign Application Priority Data

Sep. 4, 2006 (JP) ................. 2006-238753

(51) Int. Cl.
C07C 229/04 (2006.01)
C07F 9/28 (2006.01)
(52) U.S. Cl. ........................... 560/155; 562/15
(58) Field of Classification Search .............. None
See application file for complete search history.

(56) References Cited

U.S. PATENT DOCUMENTS

| | | | |
|---|---|---|---|
| 4,168,963 | A | 9/1979 | Rupp et al. |
| 4,499,027 | A | 2/1985 | Minowa et al. |
| 4,777,279 | A | 10/1988 | Zeiss |
| 4,922,006 | A | 5/1990 | Zeiss |
| 6,313,317 | B1 | 11/2001 | Sayo et al. |
| 6,686,181 | B1 | 2/2004 | Bartsch |
| 6,936,444 | B1 | 8/2005 | Bartsch |

FOREIGN PATENT DOCUMENTS

| | | |
|---|---|---|
| JP | 52-139727 | 11/1977 |
| JP | 55-00025 | 1/1980 |
| JP | 59-219297 | 12/1984 |
| JP | 62-132891 | 6/1987 |
| JP | 62-226993 | 10/1987 |
| JP | 11-269185 | 10/1999 |
| JP | 2003-505031 | 2/2003 |
| JP | 2003-528572 | 9/2003 |
| WO | 2004/035594 | 4/2004 |

OTHER PUBLICATIONS

H. Zeiss, "An Efficient Asymmertric Synthesis of Both Enantiomers of Phosphinothricin", Tetrahedron Letters, vol. 28, No. 12, pp. 1255-1258, 1987.
H. Zeiss, "Enantioselective Synthesis of L-Phosphinothricin from L-Methionine and L-Glutamic Acid via L-Vinylglycine", Tetrahedron, vol. 48, No. 38, pp. 8263-8270, 1992.
H. Zeiss, "Enantioselective Synthesis of Both Enantiomers of Phosphinothricin via Asymmetric Hydrogenation of α-Acylamido Acrylates", J. Org. Chem., vol. 56, No. 5, pp. 1783-1788, 1991.
W. Tang et al., "New Chiral Phosphorus Ligands for Enantioselective Hydrogenation", Chem. Rev., vol. 103, No. 8, pp. 3029-3069, 2003.
T. Ikariya et al., "Synthesis of Novel Chiral Ruthenium Complexes of 2,2'-Bis(diphenylphosphino)-1,1'-binaphthyl and Their Use as Asymmetric Catalyst", J. Chem. Soc., Chem. Commun., pp. 922-924, 1985.
K. Mashima et al., "Synthesis of New Cationic BINAP-Ruthenium(II) Complexes and Their Use in Asymmetric Hydrogenation [BINAP = 2,2'-bis(diphenylphosphino)-1,1'-binaphthyl]", J. Chem. Soc., Chem. Commun., pp. 1208-1210, 1989.
Extended European Search Report issued Mar. 3, 2011 in European Application No. 07806589.3.
M. Kitamura et al., "Mechanism of Asymmetric Hydrogenation of α-(Acylamino)acrylic Esters Catalyzed by BINAP-Ruthenium(II) Diacetate", J. Am. Chem. Soc., vol. 124, No. 23, pp. 6649-6667, Jun. 12, 2002.

*Primary Examiner* — Paul A Zucker
(74) *Attorney, Agent, or Firm* — Wenderoth, Lind & Ponack, L.L.P.

(57) ABSTRACT

The present invention is a process for producing optically active aminophosphinylbutanoic acids represented by the formula (2),

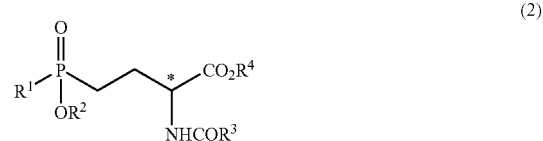

comprising asymmetrically hydrogenating a compound represented by the formula (1)

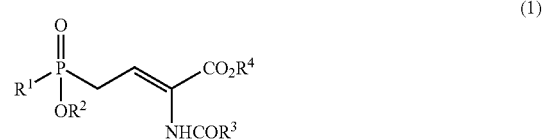

in the presence of a ruthenium-optically active phosphine complex, a process for the production thereof, and a compound useful in a herbicide such as L-AHPB that can be produced with good efficiency and high asymmetric yield.

11 Claims, No Drawings

PROCESS FOR PRODUCTION OF OPTICALLY ACTIVE AMINOPHOSPHINYLBUTANOIC ACIDS

This application is a U.S. national stage of International Application No. PCT/JP2007/067116 filed Sep. 3, 2007.

TECHNICAL FIELD

The present invention relates to a process for the production of optically active aminophosphinylbutanoic acids that are important as an intermediate of a compound useful in a herbicide such as L-2-amino-4-(hydroxymethylphosphinyl) butanoic acid (hereinafter, abbreviated as L-AHPB).

BACKGROUND ART

DL-2-amino-4-(hydroxymethylphosphinyl)butanoic acid (hereinafter, abbreviated as DL-AHPB) is a known compound having a herbicidal activity and used as an effective herbicide having a wide spectrum (Japanese Patent Application Laid-Open (JP-A) No. Sho52-139727). However, the herbicidal activity of DL-AHPB is about a half of that of L-AHPB, and it has been clear that a main substance of the herbicidal activity is L-AHPB (JP-A No. Sho55-000025 and JP-A No. Sho59-219297). Because of this, development of a process for producing L-AHPB selectively and effectively has been strongly desired.

Conventionally, as for the process for the production of L-AHPB, processes such as (a) a process with using a microorganism and an enzyme and (b) an asymmetric synthesis method are known.

As for examples of the process of (a), a process for producing L-AHPB from 4-(hydroxymethylphosphinyl)-2-oxobutanoic acid by using a transamination enzyme (Japanese Patent Application National Publication (Laid-Open) No. 2003-528572) and a process for producing L-AHPB from N-acetyl-DL-AHPB by using an enzymatic racemate resolution (Japanese Patent Application National Publication (Laid-Open) No. 2003-505031) are disclosed. However, there are problems in both of these processes being needed to carry out a reaction at a low substrate concentration, post treatment and purification steps are complicated, an expensive optically active amino acid has to be used at an equivalent mol or more in the transamination reaction, etc.

As for examples of the asymmetric synthesis of (b), a process for synthesizing L-AHPB by alkylation of (R)-3-isopropyl-2,5-dialkoxy-3,6-dihydropyrazine (JP-A No. Sho62-132891 and Tetrahedron Lett., 1255 (1987)) and a method of converting L-vinylglycine stereospecifically to L-AHPB (Tetrahedron, 8263 (1992)) are disclosed. However, it is necessary to use an expensive optically active amino acid such as D-valine and L-vinylglycine as a starting raw material, and there is a problem in the point of providing a raw material with low cost and in a large amount. Furthermore, an example of the asymmetric synthesis including a process for producing L-AHPB by an asymmetric hydrogenation reaction of 2-acetylamino-4-(hydroxymethylphosphinyl)-2-butenoic acid (JP-A No. Sho62-226993 and J. Org. Chem., 56, 1783 (1991)) is disclosed. In this process, the asymmetric hydrogenation reaction is performed using a rhodium catalyst having an optically active diphenylphosphine compound as a ligand. However, the rhodium catalyst is very expensive and catalytic efficiency is not high.

On the other hand, the asymmetric hydrogenation reaction using a rhodium catalyst from dehydroamino acid to amino acid has already been well known in general (Chem. Rev., 103, 3029-3070 (2003)). However, many of the reactions are an asymmetric reduction reaction to dehydroamino acid having an alkyl group and an aryl group in a side chain, and there are few examples of a reaction using dehydroamino acid having a substituent with high polarity in a side chain.

DISCLOSURE OF THE INVENTION

Problems to be Solved by the Invention

The objective of the present invention is to provide a process for the production of an optically active aminophosphinylbutanoic acid, that is important as an intermediate of a compound that is useful in a herbicide such as L-AHPB, with good efficiency and high enantioselectivity with using a catalytic asymmetric synthesis reaction.

Means for Solving the Problems

The present inventors performed an investigation of an asymmetric catalyst in an asymmetric hydrogenation reaction of 2-acylamino-4-(hydroxymethylphosphinyl)-2-butenoic acid. As a result of the investigation, the present inventors found that L-2-acetylamino-4-(hydroxymethylphosphinyl) butanoic acid, which is an important intermediate of L-AHPB, can be obtained with good efficiency and high asymmetric yield when a ruthenium-optically active phosphine complex is used, and completed the present invention.

The present invention is as follows.

(1) A process for producing optically active aminophosphinylbutanoic acids represented by the formula (2)

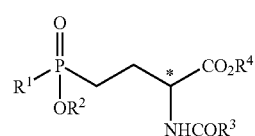

(2)

(in the formula (2), $R^1$ represents an alkyl group having 1 to 4 carbon atom(s), $R^2$ represents hydrogen atom or an alkyl group having 1 to 4 carbon atom(s), $R^3$ represents an alkyl group having 1 to 4 carbon atom(s), an alkoxy group having 1 to 4 carbon atom(s), an aryl group, an aryloxy group, or a benzyloxy group, and $R^4$ represents hydrogen atom or an alkyl group having 1 to 4 carbon atom(s); and * represents an asymmetric carbon atom), in which a compound represented by the formula (1)

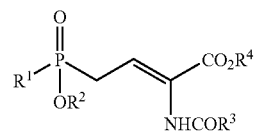

(1)

(in the formula (1), $R^1$ represents an alkyl group having 1 to 4 carbon atom(s), $R^2$ represents hydrogen atom or an alkyl group having 1 to 4 carbon atom(s), $R^3$ represents an alkyl group having 1 to 4 carbon atom(s), an alkoxy group having 1 to 4 carbon atom(s), an aryl group, an aryloxy group, or a benzyloxy group, and $R^4$ represents hydrogen atom or an alkyl group having 1 to 4 carbon atom(s)) is asymmetrically hydrogenated in the presence of a ruthenium-optically active phosphine complex.

(2) The process according to the above (1), in which an optically active phosphine compound constituting the ruthenium-optically active phosphine complex is an optically active substance of phosphine represented by the formula (3)

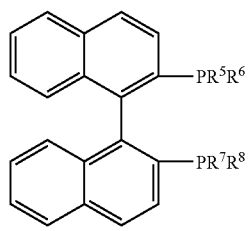

(3)

(in the formula (3), each of $R^5$, $R^6$, $R^7$, and $R^8$ independently represents a phenyl group that may be substituted with a substituent selected from a group consisting of halogen atom, a lower alkyl group, and a lower alkoxy group, a cyclopentyl group, or a cyclohexyl group) or the formula (4)

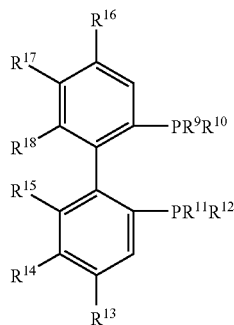

(4)

(in the formula (4), each of $R^9$, $R^{10}$, $R^{11}$, and $R^{12}$ independently represents a phenyl group that may be substituted with a substituent selected from a group consisting of halogen atom, a lower alkyl group, and a lower alkoxy group, a cyclopentyl group, or a cyclohexyl group; $R^3$, $R^{14}$, $R^{16}$, and $R^{17}$ independently represent hydrogen atom, an alkyl group, an alkoxy group, an acyloxy group, halogen atom, a haloalkyl group, or a dialkylamino group, and $R^{15}$ and $R^{18}$ represent an alkyl group, an alkoxy group, an acyloxy group, halogen atom, a haloalkyl group, or a dialkylamino group; a methylene chain that may have a substituent or a (poly)methylenedioxy group that may have a substituent may be formed in two of $R^{13}$, $R^{14}$, and $R^{15}$ and a methylene chain that may have a substituent or a (poly)methylenedioxy group that may have a substituent may be formed in two of $R^{16}$, $R^{17}$, and $R^{18}$; and further, a methylene chain that may have a substituent or a (poly)methylenedioxy group that may have a substituent may be formed in $R^{15}$ and $R^{18}$).

(3) The process according to the above (2), in which the ruthenium-optically active phosphine complex is a complex represented by the following formula (5)

$$(Ru_a W_b X_c L_d)_e Y_f Z_g \quad (5)$$

(in the formula (5), L represents the optically active substance of phosphine represented by the formula (3) or (4) as in the above (2); X represents chlorine (Cl), bromine (Br), or iodine (I); and further, combinations of values represented by a, b, c, d, e, f, and g and substances represented by W, Y, and Z are any of the combinations listed in i) to vi)):

i) a=2, b=0, c=4, d=2, e=1, f=1, g=0, and Y represents $N(CH_2CH_3)_3$;

ii) a=1, b=1, c=1, d=1, e=1, f=1, g=0, W represents benzene, p-cymene, or mesitylene, and Y represents chlorine (Cl), bromine (Br), or iodine (I);

iii) a=1, b=0, c=1, d=1, e=2, f=3, g=1, Y represents (μ-Cl), (μ-Br), or (μ-I), and Z represents $(CH_3)_2NH_2$ or $(CH_3CH_2)_2NH_2$;

iv) a=1, b=2, c=0, d=1, e=1, f=0, g=0, and W represents $CH_3CO_2$ or $CF_3CO_2$;

v) a=1, b=1, c=1, d=2, e=1, f=0, g=0, W represents hydrogen (H);

vi) a=3, b=0, c=5, d=3, e=1, f=1, g=0, Y represents chlorine (Cl), bromine (Br), or iodine (I).

Effect of the Invention

With the process for the production according to the present invention, an optically active aminophosphinylbutanoic acid that is important as an intermediate of a compound that is useful in a herbicide such as L-AHPB can be produced with good efficiency and high optical purity.

THE BEST MODE FOR CARRYING OUT THE INVENTION

The present invention is a process for producing an optically active aminophosphinylbutanoic acids represented by the formula (2)

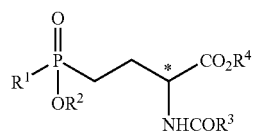

(2)

(in the formula (2), $R^1$ represents an alkyl group having 1 to 4 carbon atom(s), $R^2$ represents hydrogen atom or an alkyl group having 1 to 4 carbon atom(s), $R^3$ represents an alkyl group having 1 to 4 carbon atom(s), an alkoxy group having 1 to 4 carbon atom(s), an aryl group, an aryloxy group, or a benzyloxy group, and $R^4$ represents hydrogen atom or an alkyl group having 1 to 4 carbon atom(s); and * represents an asymmetric carbon atom). In the process for the production according to the present invention, the optically active aminophosphinylbutanoic acid represented by the above formula (2) is obtained by asymmetric hydrogenation a compound represented by the formula (1)

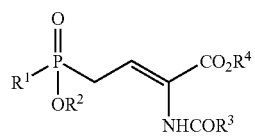

(1)

(in the formula (1), $R^1$ represents an alkyl group having 1 to 4 carbon atom(s), $R^2$ represents hydrogen atom or an alkyl group having 1 to 4 carbon atom(s), $R^3$ represents an alkyl group having 1 to 4 carbon atom(s), an alkoxy group having 1 to 4 carbon atom(s), an aryl group, an aryloxy group, or a benzyloxy group, and $R^4$ represents hydrogen atom or an alkyl group having 1 to 4 carbon atom(s)) in the presence of a ruthenium-optically active phosphine complex.

The groups represented by $R^1$, $R^2$, $R^3$, and $R^4$ in the compound represented by the formula (1) used in the present invention and the optically active aminophosphinylbutanoic acids represented by the formula (2) produced by the present invention are explained.

Specific examples of the alkyl group having 1 to 4 carbon atom(s) in $R^1$, $R^2$, $R^3$, and $R^4$ include methyl group, ethyl group, n-propyl group, isopropyl group, n-butyl group, 2-butyl group, isobutyl group, and t-butyl group.

Specific examples of the alkoxy group having 1 to 4 carbon atom(s) in $R^3$ include methoxy group, ethoxy group, n-propoxy group, isopropoxy group, n-butoxy group, 2-butoxy group, isobutoxy group, and t-butoxy group. Specific examples of the aryl group in $R^3$ include phenyl group, naphthyl group, and anthryl group. Specific examples of the aryloxy group in $R^3$ include phenyloxy group, naphthyloxy group, and anthryloxy group.

The compound represented by the formula (1) can be synthesized, for example, with the method described in JP-A No. Sho62-226993 or J. Org. Chem., 56, 1783 (1991).

Further, a compound in which $R^1$ is methyl group, $R^2$ and $R^4$ are hydrogen atom, and $R^3$ is an alkyl group having 1 to 4 carbon atom(s), an alkoxy group having 1 to 4 carbon atom(s), or a benzyloxy group is preferable among the compounds represented by the formula (1).

Specific examples of the compounds represented by the formula (1) include the compounds shown below.
2-acetylamino-4-(hydroxymethylphosphinyl)-2-butenoic acid,
2-acetylamino-4-(ethoxy(methyl)phosphinyl)-2-butenoic acid,
2-propionylamino-4-(hydroxymethylphosphinyl)-2-butenoic acid,
2-benzonylamino-4-(hydroxymethylphosphinyl)-2-butenoic acid,
2-t-butoxycarbonylamino-4-(hydroxymethylphosphinyl)-2-butenoic acid,
2-benzyloxycarbonylamino-4-(hydroxymethylphosphinyl)-2-butenoic acid,
2-propionylamino-4-(methoxy(methyl)phosphinyl)-2-butenoic acid,
2-benzoylamino-4-(methoxy(methyl)phosphinyl)-2-butenoic acid,
2-benzoylamino-4-(ethoxy(methyl)phosphinyl)-2-butenoic acid,
2-t-butoxycarbonylamino-4-(methoxy(methyl)phosphinyl)-2-butenoic acid,
2-acetylamino-4-(hydroxymethylphosphinyl)-2-butenoic acid methyl ester,
2-propionylamino-4-(hydroxymethylphosphinyl)-2-butenoic acid methyl ester,
2-benzoylamino-4-(hydroxymethylphosphinyl)-2-butenoic acid methyl ester,
2-t-butoxycarbonylamino-4-(hydroxymethylphosphinyl)-2-butenoic acid methyl ester,
2-benzyloxycarbonylamino-4-(hydroxymethylphosphinyl)-2-butenoic acid methyl ester,
2-propionylamino-4-(methoxy(methyl)phosphinyl)-2-butenoic acid methyl ester,
2-benzoylamino-4-(methoxy(methyl)phosphinyl)-2-butenoic acid methyl ester,
2-t-butoxycarbonylamino-4-(methoxy(methyl)phosphinyl)-2-butenoic acid methyl ester,
2-acetylamino-4-(hydroxymethylphosphinyl)-2-butenoic acid ethyl ester,
2-propionylamino-4-(hydroxymethylphosphinyl)-2-butenoic acid ethyl ester,
2-benzoylamino-4-(hydroxymethylphosphinyl)-2-butenoic acid ethyl ester,
2-t-butoxycarbonylamino-4-(hydroxymethylphosphinyl)-2-butenoic acid ethyl ester,
2-benzyloxycarbonylamino-4-(hydroxymethylphosphinyl)-2-butenoic acid ethyl ester,
2-propionylamino-4-(methoxy(methyl)phosphinyl)-2-butenoic acid ethyl ester,
2-benzoylamino-4-(methoxy(methyl)phosphinyl)-2-butenoic acid ethyl ester,
2-t-butoxycarbonylamino-4-(methoxy(methyl)phosphinyl)-2-butenoic acid ethyl ester,
2-benzyloxycarbonylamino-4-(ethoxy(methyl)phosphinyl)-2-butenoic acid methyl ester,
2-benzyloxycarbonylamino-4-(ethoxy(methyl)phosphinyl)-2-butenoic acid ethyl ester,
2-t-butoxycarbonylamino-4-(ethoxy(methyl)phosphinyl)-2-butenoic acid methyl ester,
2-t-butoxycarbonylamino-4-(ethoxy(methyl)phosphinyl)-2-butenoic acid ethyl ester,
2-benzoylamino-4-(ethoxy(methyl)phosphinyl)-2-butenoic acid methyl ester,
2-benzoylamino-4-(ethoxy(methyl)phosphinyl)-2-butenoic acid ethyl ester,
2-acetylamino-4-(ethoxy(methyl)phosphinyl)-2-butenoic acid methyl ester, and
2-acetylamino-4-(ethoxy(methyl)phosphinyl)-2-butenoic acid ethyl ester.

The ruthenium-optically active phosphine complex used in the present invention includes a complex obtained from a ruthenium compound, an optically active phosphine compound, and, if desired, a neutral organic coordinated compound or an amine compound.

The above-described ruthenium compound may be a ruthenium compound normally used in this art, and there is exemplified ruthenium halide such as $RuCl_3$, $RuBr_3$, and $RuI_3$, and its hydrates, and a complex such as $(RuCl_2(benzene))_2$, $(RuBr_2(benzene))_2$, $(RuI_2(benzene))_2$, $(RuCl_2(p\text{-}cymene))_2$, $(RuBr_2(p\text{-}cymene))_2$, $(RuI_2(p\text{-}cymene))_2$, $(RuCl_2(cod))_n$, $(RuBr_2(cod))_n$, and $(RuI_2(cod))_n$. (The above-described "cod" represents 1,5-cyclooctadiene. The same applies hereinafter.)

The above-described optically active phosphine compound may be an optically active phosphine compound normally used in this art, and its example includes a phosphine compound having bidentate coordination property, and further preferably an optically active phosphine compound having axial asymmetry.

In the present invention, the optically active phosphine compound preferably used to obtain the above-described ruthenium-optically active phosphine complex includes an optically active substance of phosphine represented by the formula (3)

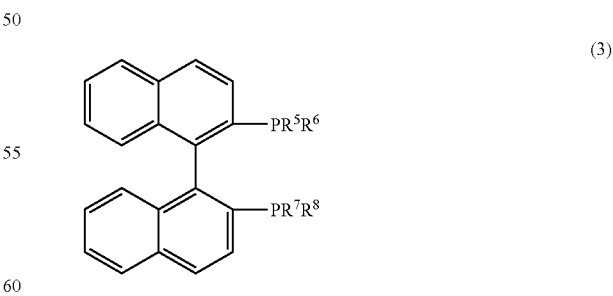

(3)

(in the formula (3), each of $R^5$, $R^6$, $R^7$, and $R^8$ independently represents a phenyl group that may be substituted with a substituent selected from a group consisting of halogen atom, a lower alkyl group, and a lower alkoxy group, a cyclopentyl group, or a cyclohexyl group) and an optically active substance of phosphine represented by the formula (4)

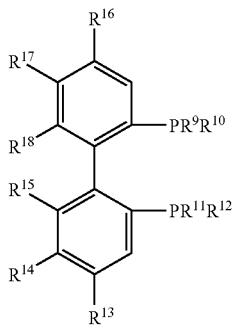

(4)

(in the formula (4), each of $R^9$, $R^{10}$, $R^{11}$, and $R^{12}$ independently represents a phenyl group that may be substituted with a substituent selected from a group consisting of halogen atom, a lower alkyl group, and a lower alkoxy group, a cyclopentyl group, or a cyclohexyl group; $R^{13}$, $R^{14}$, $R^{16}$, and $R^{17}$ independently represent hydrogen atom, an alkyl group, an alkoxy group, an acyloxy group, halogen atom, a haloalkyl group, or a dialkylamino group, and $R^{15}$ and $R^{18}$ represent an alkyl group, an alkoxy group, an acyloxy group, halogen atom, a haloalkyl group, or a dialkylamino group; a methylene chain that may have a substituent or a (poly)methylenedioxy group that may have a substituent may be formed in two of $R^{13}$, $R^{14}$, and $R^{15}$ and a methylene chain that may have a substituent or a (poly)methylenedioxy group that may have a substituent may be formed in two of $R^{16}$, $R^{17}$, and $R^{18}$; and further, a methylene chain that may have a substituent or a (poly)methylenedioxy group that may have a substituent may be formed in $R^{15}$ and $R^{18}$).

Hereinafter, each substituent in the formulas (3) and (4) is explained.

In the formulas (3) and (4), "a phenyl group that may be substituted with a substituent selected from a group consisting of halogen atom, a lower alkyl group, and a lower alkoxy group" represented by $R^5$, $R^6$, $R^7$, $R^8$, $R^9$, $R^{10}$, $R^{11}$, and $R^{12}$ is either phenyl group or a phenyl group substituted with a substituent, and the substituent is halogen atom, a lower alkyl group, or a lower alkoxy group. An example of the phenyl group substituted with a substituent includes a phenyl group in which one or two hydrogen atoms of the phenyl group is substituted with the above-described substituent. In the case that the above-described substituent is two or more, they may be the same or may be different.

Examples of the halogen atom as the above-described substituent include fluorine atom, chlorine atom, bromine atom, and iodine atom, and particularly fluorine atom is preferable. Examples of the above-described lower alkyl group are a linear, a branched, or a cyclic alkyl group having 1 to 6 carbon atom(s), preferably 1 to 4 carbon atom(s). Further, Examples of the above-described lower alkoxy group are a linear, a branched, or a cyclic alkoxy group having 1 to 6 carbon atom(s), preferably 1 to 4 carbon atom(s).

With regard to the lower alkyl group as a substituent on the phenyl group in $R^5$, $R^6$, $R^7$, and $R^8$, for example, there is exemplified an alkyl group having 1 to 6 carbon atom(s) that may be a linear chain or branched such as methyl group, ethyl group, n-propyl group, isopropyl group, n-butyl group, isobutyl group, 2-butyl group, and tert-butyl group. With regard to the lower alkoxy group as the substituent, for example, there is exemplified an alkoxy group having 1 to 6 carbon atom(s) that may be a linear chain or branched such as methoxy group, ethoxy group, n-propoxy group, isopropoxy group, n-butoxy group, isobutoxy group, 2-butoxy group, and t-butoxy group. With regard to the halogen atom as the substituent, for example, there is exemplified halogen atom such as chlorine atom, bromine atom, and fluorine atom. Specific examples of the group represented by $R^5$, $R^6$, $R^7$, and $R^8$ include phenyl group, p-tolyl group, m-tolyl group, 3,5-xylyl group, p-t-butylphenyl group, p-methoxyphenyl group, 4-methoxy-3,5-di(t-butyl)phenyl group, 4-methoxy-3,5-dimethylphenyl group, p-chlorophenyl group, cyclopentyl group, and cyclohexyl group.

Specific examples of the optically active phosphine compound represented by the formula (3) include
2,2'-bis(diphenylphosphino)-1,1'-binaphthyl (hereinafter referred to as binap),
2,2'-bis(di(p-tolyl)phosphino)-1,1'-binaphthyl (hereinafter referred to as t-binap),
2,2'-bis(di(m-tolyl)phosphino)-1,1'-binaphthyl,
2,2'-bis(di(3,5-xylyl)phosphino)-1,1'-binaphthyl (hereinafter referred to as dm-binap),
2,2'-bis(di(p-t-butylphenyl)phosphino)-1,1'-binaphthyl,
2,2'-bis(di(p-methoxyphenyl)phosphino)-1,1'-binaphthyl,
2,2'-bis(di(3,5-di-t-butyl-4-methoxyphenyl)phosphino)-1,1'-binaphthyl,
2,2'-(bis(di(cyclopentyl)phosphino)-1,1'-binaphthyl, and
2,2'-bis(di(cyclohexyl)phosphino)-1,1'-binaphthyl. Among these, binap or t-binap is more preferable.

With regard to the lower alkyl group as a substituent on the phenyl group in $R^9$ to $R^{12}$, for example, there is exemplified an alkyl group having 1 to 6 carbon atom(s) that may be a linear chain or branched such as methyl group and tert-butyl group. With regard to the lower alkoxy group as the substituent, for example, there is exemplified an alkoxy group having 1 to 6 carbon atom(s) that may be a linear chain or branched such as methoxy group and tert-butoxy group. With regard to the halogen atom as the substituent, for example, there is exemplified chlorine atom, bromine atom, and fluorine atom. These substituents may substitute a plurality of sites on the phenyl group.

Specific examples as $R^9$, $R^{10}$, $R^{11}$, and $R^{12}$ include phenyl group, p-tolyl group, m-tolyl group, o-tolyl group, 3,5-xylyl group, 3,5-di-t-butylphenyl group, p-t-butylphenyl group, p-methoxyphenyl group, 3,5-di-t-butyl-4-methoxyphenyl group, p-chlorophenyl group, m-fluorophenyl group, cyclopentyl group, and cyclohexyl group.

With regard to the alkyl group represented by $R^{13}$ to $R^{18}$, for example, there is exemplified an alkyl group having 1 to 6 carbon atom(s) that may be a linear chain or branched such as methyl group and t-butyl group. With regard to the alkoxy group, for example, there is exemplified an alkoxy group having 1 to 6 carbon atom(s) that may be a linear chain or branched such as methoxy group and t-butoxy group. With regard to the acyloxy group, for example, there is exemplified acetoxy group, propanoyloxy group, trifluoroacetoxy group, and benzoyloxy group. With regard to the halogen atom, for example, there is exemplified chlorine atom, bromine atom, and fluorine atom. With regard to the haloalkyl group, for example, there is exemplified a haloalkyl group having 1 to 4 carbon atom(s) such as trifluoromethyl group. With regard to the dialkylamino group, for example, there is exemplified dimethylamino group and diethylamino group.

The methylene chain in "a methylene chain that may have a substituent" of the case of forming a methylene chain that may have a substituent in two of $R^{13}$, $R^{14}$, and $R^{15}$, the case of forming a methylene chain that may have a substituent in two of $R^{16}$, $R^{17}$, and $R^{18}$, and the case of forming a methylene chain that may have a substituent in two of $R^{15}$ and $R^{18}$ is preferably a methylene chain having 3 to 5 carbon atoms, and its specific examples include trimethylene group, tetramethylene group, and pentamethylene group. Further, the substituent in "a methylene chain that may have a substituent" includes an alkyl group and halogen atom, and its specific examples include the alkyl group having 1 to 6 carbon atom(s) as described above (for example, methyl group, ethyl group, n-propyl group, isopropyl group, n-butyl group, isobutyl group, 2-butyl group, tert-butyl group, etc.), chlorine atom, bromine atom, and fluorine atom.

The (poly)methylenedioxy group in "a (poly)methylenedioxy group that may have a substituent" in the case of forming a (poly)methylenedioxy group that may have a substituent in two of $R^{13}$, $R^{14}$, and $R^{15}$, the case of forming a (poly)methylenedioxy group that may have a substituent in two of $R^{16}$, $R^{17}$, and $R^{18}$, and the case of forming a (poly)methylenedioxy group that may have a substituent in two of $R^{15}$ and $R^{18}$ is preferably a (poly)methylenedioxy group having 1 to 3 carbon atom(s), and its specific examples include methylenedioxy group, ethylenedioxy group, and trimethylenedioxy group. Further, the substituent in "a (poly)methylenedioxy group that may have a substituent" include an alkyl group and halogen atom, and its specific examples include the alkyl group having 1 to 6 carbon atom(s) as described above (for example, methyl group, ethyl group, n-propyl group, isopropyl group, n-butyl group, isobutyl group, 2-butyl group, tert-butyl group, etc.), chlorine atom, bromine atom, and fluorine atom. Specific groups of the (poly)methylenedioxy group substituted with an alkyl group or halogen atom include propane-2,2-diyldioxy group, butane-2,3-diyldioxy group, and difluoromethylenedioxy group.

Specific examples of the optically active phosphine compound represented by the formula (4) are not limited to the following compounds, but include
2,2'-bis(diphenylphosphino)-5,5',6,6',7,7',8,8'-octahydro-1,1'-binaphthyl,
2,2'-bis(di-p-tolylphosphino)-5,5',6,6',7,7',8,8'-octahydro-1,1'-binaphthyl,
2,2'-bis(di-m-tolylphosphino)-5,5',6,6',7,7',8,8'-octahydro-1,1'-binaphthyl,
2,2'-bis(di-3,5-xylylphosphino)-5,5',6,6',7,7',8,8'-octahydro-1,1'-binaphthyl,
2,2'-bis(di-p-tertiarybutylphenylphosphino)-5,5',6,6',7,7',8,8'-octahydro-1,1'-binaphthyl,
2,2'-bis(di-p-methoxyphenylphosphino)-5,5',6,6',7,7',8,8'-octahydro-1,1'-binaphthyl,
2,2'-bis(di-p-chlorophenylphosphino)-5,5',6,6',7,7',8,8'-octahydro-1,1'-binaphthyl,
2,2'-bis(dicyclopentylphosphino)-5,5',6,6',7,7',8,8'-octahydro-1,1'-binaphthyl,
2,2'-bis(dicyclohexylphosphino)-5,5',6,6',7,7',8,8'-octahydro-1,1'-binaphthyl,
((4,4'-bi-1,3-benzodioxole)-5,5'-diyl)bis(diphenylphosphine) (hereinafter referred to as segphos),
((4,4'-bi-1,3-benzodioxole)-5,5'-diyl)bis(bis(3,5-dimethylphenyl)phosphine),
((4,4'-bi-1,3-benzodioxole)-5,5'-diyl)bis(bis(3,5-di-t-butyl-4-methoxyphenyl)phosphine),
((4,4'-bi-1,3-benzodioxole)-5,5'-diyl)bis(bis(4-methoxyphenyl)phosphine),
((4,4'-bi-1,3-benzodioxole)-5,5'-diyl)bis(dicyclohexylphosphine),
((4,4'-bi-1,3-benzodioxole)-5,5'-diyl)bis(bis(3,5-di-t-butylphenyl)phosphine),
2,2'-bis(diphenylphosphino)-4,4',6,6'-tetramethyl-5,5'-dimethoxy-1,1'-biphenyl,
2,2'-bis(di-p-methoxyphenylphosphino)-4,4',6,6'-tetramethyl-5,5'-dimethoxy-1,1'-biphenyl,
2,2'-bis(diphenylphosphino)-4,4',6,6'-tetra(trifluoromethyl)-5,5'-dimethyl-1,1'-biphenyl,
2,2'-bis(diphenylphosphino)-4,6-di(trifluoromethyl)-4',6'-dimethyl-5'-methoxy-1,1'-biphenyl,
2-dicyclohexylphosphino-2'-diphenylphosphino-4,4',6,6'-tetramethyl-5,5'-dimethoxy-1,1'-biphenyl,
2,2'-bis(diphenylphosphino)-6,6'-dimethyl-1,1'-biphenyl,
2,2'-bis(diphenylphosphino)-4,4',6,6'-tetramethyl-1,1'-biphenyl,
2,2'-bis(diphenylphosphino)-3,3',6,6'-tetramethyl-1,1'-biphenyl,
2,2'-bis(diphenylphosphino)-4,4'-difluoro-6,6'-dimethyl-1,1'-biphenyl,
2,2'-bis(diphenylphosphino)-4,4'-bis(dimethylamino)-6,6'-dimethyl-1,1'-biphenyl,
2,2'-bis(di-p-tolylphosphino)-6,6'-dimethyl-1,1'-biphenyl,
2,2'-bis(di-o-tolylphosphino)-6,6'-dimethyl-1,1'-biphenyl,
2,2'-bis(di-m-fluorophenylphosphino)-6,6'-dimethyl-1,1'-biphenyl,
1,11-bis(diphenylphosphino)-5,7-dihydrobenzo(c,e)oxepin,
2,2'-bis(diphenylphosphino)-6,6'-dimethoxy-1,1'-biphenyl,
2,2'-bis(diphenylphosphino)-5,5',6,6'-tetramethoxy-1,1'-biphenyl,
2,2'-bis(di-p-tolylphosphino)-6,6'-dimethoxy-1,1'-biphenyl, and
2,2'-bis(diphenylphosphino)-4,4',5,5',6,6'-hexamethoxy-1,1'-biphenyl.

Furthermore, examples of the optically active phosphine compound which can be used in the present invention other than the compound represented by the formulas (3) and (4) include N,N-dimethyl-1-(1',2-bis(diphenylphosphino)ferrocenyl)ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis((o-methoxyphenyl)phenylphosphino)ethane, 1,2-bis(2,5-dimethylphosphorano)benzene, 1,2-bis(2,5-diisopropylphosphorano)benzene, 1,2-bis(2,5-dimethylphosphorano)ethane, 1-(2,5-dimethylphosphorano)-2-(diphenylphosphino)benzene, 5,6-bis(diphenylphosphino)-2-norbornene, N,N'-bis(diphenylphosphino)-N,N'-bis(1-phenylethyl)ethylene diamine, 1,2-bis(diphenylphosphino)propane, and 2,4-bis(diphenylphosphino)pentane. The optically active phosphine compound that can be used in the present invention is not limited to these at all.

Furthermore, examples of the neutral organic coordinated compound to be used with desire to obtain the ruthenium-optically active complex according to the present invention include nonconjugated diene such as 1,5-cyclooctadiene (hereinafter referred to as cod) and norbornadiene (hereinafter referred to as nbd); a benzene derivative such as benzene, p-cymene, and mesitylene; N,N-dimethylformamide; and acetonitrile, and examples of the amine compound include a tri-lower alkylamine (for example, trimethyamine, triethylamine, etc.), a di-lower alkylamine (for example, dimethylamine, diethylamine, etc.), and pyridine.

The ruthenium-optically active phosphine complex used in the present invention is preferably a complex represented by the following formula (5)

(in the formula (5), L represents the optically active substance of phosphine represented by the above-described formula (3) or (4); X represents chlorine (Cl), bromine (Br), or iodine (I); and further, combinations of values represented by a, b, c, d, e, f, and g and substances represented by W, Y, and Z are any of the combinations listed in i) to vi)).

i) a=2, b=0, c=4, d=2, e=1, f=1, g=0, and Y represents $N(CH_2CH_3)_3$.

ii) a=1, b=1, c=1, d=1, e=1, f=1, g=0, W represents benzene, p-cymene, or mesitylene, and Y represents chlorine (Cl), bromine (Br), or iodine (I).

iii) a=1, b=0, c=1, d=1, e=2, f=3, g=1, Y represents (μ-Cl), (μ-Br), or (μ-I), and Z represents $(CH_3)_2NH_2$ or $(CH_3CH_2)_2NH_2$.

iv) a=1, b=2, c=0, d=1, e=1, f=0, g=0, and W represents $CH_3CO_2$ or $CF_3CO_2$.

v) a=1, b=1, c=1, d=2, e=1, f=0, g=0, W represents hydrogen (H).

vi) a=3, b=0, c=5, d=3, e=1, f=1, g=0, Y represents chlorine (Cl), bromine (Br), or iodine (I).

Examples of the ruthenium-optically active phosphine complex used in the present invention are the following. However, they are not limited to these.
$Ru(OAc)_2(L^*)$, $Ru(OCOCF_3)(L^*)$, $Ru_2Cl_4(L^*)_2NEt_3$, $((RuCl(L^*))_2(\mu-Cl)_3)(Me_2NH_2)$, $((RuCl(L^*))_2(\mu-Cl)_3)(Et_2NH_2)$, $RuCl_2(L^*)$, $RuBr_2(L^*)$, $RuI_2(L^*)$, $RuCl_2(L^*)(pyridine)_2$, $RuBr_2(L^*)(pyridine)_2$, $RuI_2(L)(pyridine)_2$, $(RuCl(benzene)(L^*))Cl$, $(RuBr(benzene)(L^*))Br$, $(RuI(benzene)(L^*))I$, $(RuCl(p-cymene)(L^*))Cl$, $(RuBr(p-cymene)(L^*))Br$, $(RuI(p-cymene)(L^*))I$, $(RuCl(mesitylene)(L^*))Cl$, $(RuBr(mesitylene)(L^*))Br$, $(RuI(mesitylene)(L^*))I$, $(Ru(L^*))(OTf)_2$, $(Ru(L^*))(BF_4)_2$, $(Ru(L^*))(ClO_4)_2$, $(Ru(L^*))(SbF_6)_2$, $(Ru(L^*))(PF_6)_2$, $Ru_3Cl_5(L^*)_3$, and $RuHCl(L^*)_2$
(In the following description and the above-described examples of the ruthenium-optically active phosphine complex, L* represents an optically active phosphine compound, Ac represents acetyl group, Et represents ethyl group, Me represents methyl group, and Tf represents trifluoromethanesulfonyl group.)

The ruthenium-optically active phosphine complex used in the present invention is produced using a well-known method. For example, it can be prepared by heating reflux on $(Ru(cod) Cl_2)_n$ and an optically active phosphine compound in a toluene solvent in the presence of trialkylamine as described in J. Chem. Soc., Chem. Commun., 922 (1985). Further, it can be prepared by heating reflux on $(Ru(benzene)Cl_2)_2$ and an optically active phosphine compound in tetrahydrofuran in the presence of dialkylamine with the method described in JP-A No. Heill-269185. Further, it can be prepared by heating reflux on $(Ru(p-cymene)I_2)_2$ and an optically active phosphine compound in methylene chloride and ethanol with the method described in J. Chem. Soc., Chem. Commun., 1208 (1989).

The reaction of asymmetric hydrogenation carried out in the process for the production according to the present invention is a hydrogen addition reaction, and can be carried out a reaction of the compound represented in the formula (1) with hydrogen gas in the presence of the ruthenium-optically active phosphine complex. The amount of the ruthenium-optically active phosphine complex used differs depending on the reaction condition, the type of the ruthenium-optically active phosphine complex, etc. However, it is normally about 1/50 to 1/100000 in a molar ratio to aminophosphinylbutenoic acids represented by the formula (1), and preferably in the range of about 1/200 to 1/10000.

Further, the hydrogenation according to the present invention can be carried out preferably in a solvent. The solvent is preferably a solvent that can dissolve a substrate and a catalyst, and its specific examples include aromatic hydrocarbons such as toluene and xylene; aliphatic hydrocarbons such as hexane and heptanes; halogenated hydrocarbons such as methylene chloride and chlorobenzene; ethers such as diethylether, tetrahydrofuran, and 1,4-dioxane; alcohols such as methanol, ethanol, isopropanol, and n-butanol; esters such as ethylacetate and butylacetate; nitriles such as acetonitrile; amides such as N,N-dimethylformamide and N-methylpyrrolidone; amines such as pyridine and triethylamine; and water. Each of these solvents may be used independently or two or more may be mixed and used. The amount of the solvent used can be selected appropriately depending on the reaction condition, etc.

The hydrogen pressure in the hydrogenation according to the present invention is normally about 0.1 to 10 MPa, and preferably 1 to 5 MPa. The reaction temperature naturally differs depending on the type of the catalyst, etc. However, it is normally about 5 to 150° C., and preferably about 30 to 100° C. The reaction time naturally differs depending on the reaction condition. However, it is normally about 5 to 30 hours.

Further, a base compound can be used in the present invention depending on necessity. The base compound used in the present invention is not especially limited but includes carbonate of an alkaline metal or an alkaline earth metal such as a lithium carbonate, sodium carbonate, potassium carbonate, rubidium carbonate, cesium carbonate, magnesium carbonate, calcium carbonate, and barium carbonate; alkaline metal alkoxide or alkaline metal phenoxide such as sodium methoxide, sodium ethoxide, sodium phenoxide, sodium t-butoxide, potassium methoxide, potassium ethoxide, potassium phenoxide, potassium t-butoxide, lithium methoxide, lithium ethoxide, lithium phenoxide, and lithium t-butoxide; hydroxide of an alkaline metal or an alkaline earth metal such as sodium hydroxide, potassium hydroxide, lithium hydroxide, barium hydroxide, and calcium hydroxide.

The amount of the base compound used is about 0.05 to 2 times mole, and preferably about 0.1 to 1.5 times mole based on the mole number of the compound represented by the formula (1).

The optically active aminophosphinylbutanoic acids represented in the formula (2) are obtained in the above-described manner. With regard to the configuration of the compound, R isomer or an S isomer can be produced by appropriately selecting the configuration of the optically active phosphine of the used ruthenium-optically active phosphine complex.

EXAMPLES

The present invention will now be more specifically illustrated by way of the following Examples, although the present invention is not limited to thereby at all. Moreover, the analytical condition in Examples is as follows.

(Analytical Condition)

Conversion rate: $^1$H-NMR and an ODS column

Optical purity: a chiral column

Example 1

Production of (S)-2-acetylamino-4-hydroxymethylphosphinylbutanoic acid

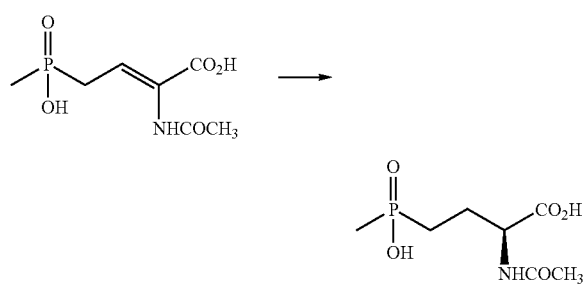

(Z)-2-acetylamino-4-hydroxymethylphosphinyl-2-butenoic acid (4.0 g, 18 mmol), (RuCl(p-cymene)((S)-binap)Cl (8.4 mg, 0.009 mmol), and methanol (20 ml) were added to a 200 ml autoclave, and a nitrogen substitution and a hydrogen substitution were performed. The temperature in the autoclave was set to 70° C., hydrogen gas was charged to 1 MPa, and the reaction solution was stirred at the same temperature for 5 hours. A part of the reaction solution was taken as a sample. After completion of the reaction was confirmed with high performance liquid chromatography (HPLC) analysis on the sample, reaction solution was cooled to room temperature, hydrogen was purged, and then the reaction solution was moved to a 100 ml flask. After methanol was removed in vacuo and water (20 ml) was added, the water phase was washed with toluene (10 ml) twice and 24.6 g of (S)-2-acetylamino-4-hydroxymethylphosphinylbutanoic acid was obtained as a solution. The optical purity of the obtained (S)-2-acetylamino-4-hydroxymethylphosphinylbutanoic acid was 90.8% ee.

Further, when the solution obtained above was concentrated, 3.8 g of a viscous yellow liquid was obtained. Moreover, the conversion rate was 100%.

Examples 2 to 4

Production of (S)-2-acetylamino-4-hydroxymethylphosphinylbutanoic acid

It was carried out in the same manner as Example 1 except that the used amount of (RuCl(p-cymene)((S)-binap)Cl was two times and the reaction time and the reaction temperature were changed as shown in Table 1. These results are shown in Table 1 below. Further, the conversion rate was 100% in all examples.

TABLE 1

| EXAMPLE | REACTION TEMPERATURE | REACTION TIME | OPTICAL PURITY (ee) |
|---|---|---|---|
| 2 | 60° C. | 17 HOURS | 91.7% |
| 3 | 70° C. | 17 HOURS | 92.8% |
| 4 | 90° C. | 17 HOURS | 91.0% |

Example 5

Production of (R)-2-acetylamino-4-hydroxymethylphosphinylbutanoic acid

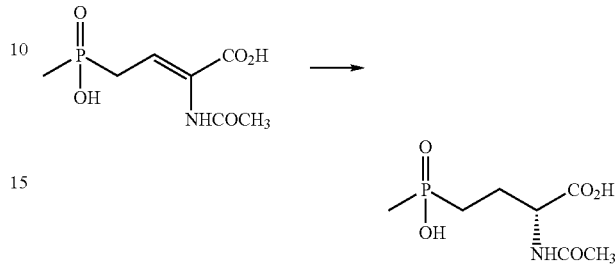

(Z)-2-acetylamino-4-hydroxymethylphosphinyl-2-butenoic acid (4.0 g, 18 mmol), (RuCl((R)-segphos)$_2$(μ-Cl)$_3$(Et$_2$NH$_2$) (0.150 g, 0.09 mmol), and methanol (40 ml) were added to a 200 ml autoclave, and a nitrogen substitution and a hydrogen substitution were performed. The temperature in the autoclave was set to 70° C., hydrogen gas was charged to 1 MPa, and the reaction solution was stirred at the same temperature for 5 hours. A part of the reaction solution was taken as a sample. After completion of the reaction was confirmed with HPLC analysis on the sample, reaction solution was cooled to room temperature, hydrogen was released, and then the reaction solution was moved to a 100 ml flask. After methanol was removed in vacuo and adding water (20 ml), the water phase was washed with toluene (10 ml) twice and a solution of (R)-2-acetylamino-4-hydroxymethylphosphinylbutanoic acid was obtained. The optical purity of the obtained (R)-2-acetylamino-4-hydroxymethylphosphinylbutanoic acid was 92.8% ee. Further, the conversion rate was 100%.

Example 6

Production of (S)-2-acetylamino-4-hydroxymethylphosphinylbutanoic acid

It was carried out in the same manner as Example 1 except that the used amount of (RuCl(p-cymene)((S)-binap)Cl was two times and 1 equivalent of sodium methoxide (NaOMe) to a hydrogenated substrate was added in the reaction system. As the result, (S)-2-acetylamino-4-hydroxymethylphosphinylbutanoic acid was obtained with the optical purity of 95.3% ee. Further, the conversion rate was 100%.

Examples 7 to 9

Production of (R)-2-acetylamino-4-hydroxymethylphosphinylbutanoic acid

It was carried out in the same manner as Example 1 except that the ruthenium-optically active phosphine complex was changed and various additives (1 equivalent to the hydrogenated substrate) were added in the reaction system as shown in Table 2. These results are shown in Table 2 below. Further, the conversion rate was 100% in all examples.

TABLE 2

| EXAMPLE | COMPLEX | ADDITIVE | OPTICAL PURITY (ee) |
|---|---|---|---|
| 7 | [RuCl{(R)-segphos}]$_2$(μ-Cl)$_3$[Et$_2$NH$_2$] | K$_2$CO$_3$ | 93.7 |
| 8 | [RuCl{(R)-t-binap}]$_2$(μ-Cl)$_3$[Et$_2$NH$_2$] | NaOMe | 94.1 |
| 9 | [RuCl(p-cymene){(R)-binap}]Cl | NaOMe | 93.1 | p-cymene

Example 10

Production of (S)-2-acetylamino-4-hydroxymethylphosphinylbutanoic acid (Z)-2-acetylamino-4-hydroxymethylphosphinyl-2-butenoic acid (5.0 g, 22.5 mmol), (RuCl(p-cymene)((S)-binap)Cl (5.2 mg, 0.0056 mmol), n-butanol (10 ml), water (15 ml), and sodium carbonate (240 mg) were added to a 100 ml autoclave, and a nitrogen substitution and a hydrogen substitution were performed. The temperature in the autoclave was set to 90° C., hydrogen gas was charged to 1 MPa, and the reaction solution was stirred at the same temperature for 6 hours. Completion of the reaction was confirmed by taking a part of the reaction solution as a sample. The optical purity of the obtained (S)-2-acetylamino-4-hydroxymethylphosphinylbutanoic acid was 90.4% ee.

Example 11

Production of (S)-2-acetylamino-4-hydroxymethylphosphinylbutanoic acid methyl ester (Z)-2-acetylamino-4-hydroxymethylphosphinyl-2-butenoic acid methyl ester (4.9 g, 19.8 mmol), (RuCl(p-cymene)((S)-binap)Cl (1.8 mg, 0.0019 mmol), and methanol (20 ml) were added to a 100 ml autoclave, and a nitrogen substitution and a hydrogen substitution were performed. The temperature in the autoclave was set to 90° C., hydrogen gas was charged to 1 MPa, and the reaction solution was stirred at the same temperature for 4 hours. Completion of the reaction was confirmed by taking a part of the reaction solution as a sample. The optical purity of the obtained (S)-2-acetylamino-4-hydroxymethylphosphinylbutanoic acid methyl ester was 90.9% ee.

Example 12

Production of (S)-2-acetylamino-4-hydroxymethylphosphinylbutanoic acid methyl ester (Z)-2-acetylamino-4-hydroxymethylphosphinyl-2-butenoic acid methyl ester (46.1 g, 185.0 mmol), (RuCl(p-cymene)(S)-binap)Cl (1.7 mg, 0.0018 mmol), and methanol (92 ml) were added to a 300 ml autoclave, and a nitrogen substitution and a hydrogen substitution were performed. The temperature in the autoclave was set to 90° C., hydrogen gas was charged to 1 MPa, and the reaction solution was stirred at the same temperature for 5 hours. Completion of the reaction was confirmed by taking a part of the reaction solution as a sample. The optical purity of the obtained (S)-2-acetylamino-4-hydroxymethylphosphinylbutanoic acid methyl ester was 90.3% ee.

INDUSTRIAL APPLICABILITY

The present invention is to stereoselectively synthesize optically active amino phosphinylbutanoic acids that is important as an intermediate of the compound useful as a herbicide such as L-AHPB by performing an asymmetric hydrogenation reaction on the compound represented by the formula (1) using a ruthenium-optically active phosphine complex as a catalyst, and superior as a process that can synthesize with lower expense, good efficiency, and high selectiveness compared to the conventional synthesis process of an optical active substance.

The invention claimed is:

1. A process for producing optically active aminophosphinylbutanoic acids represented by the formula (2):

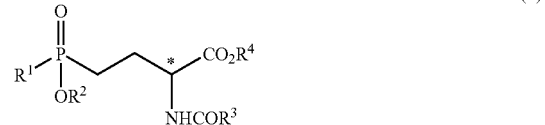

(2)

wherein $R^1$ represents an alkyl group having 1 to 4 carbon atom(s), $R^2$ represents a hydrogen atom or an alkyl group having 1 to 4 carbon atom(s), $R^3$ represents an alkyl group having 1 to 4 carbon atom(s), an alkoxy group having 1 to 4 carbon atom(s),
an aryl group, an aryloxy group, or a benzyloxy group, and $R^4$ represents a hydrogen atom or an alkyl group having 1 to 4 carbon atom(s); and * represents an asymmetric carbon atom, comprising asymmetrically hydrogenating a compound represented by the formula (1):

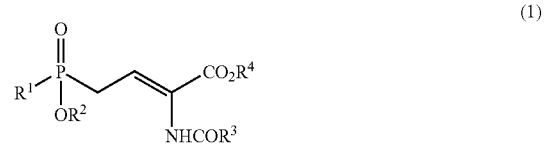

(1)

wherein $R^1$ represents an alkyl group having 1 to 4 carbon atom(s), $R^2$ represents a hydrogen atom or an alkyl group having 1 to 4 carbon atom(s), $R^3$ represents an alkyl group having 1 to 4 carbon atom(s), an alkoxy group having 1 to 4 carbon atom(s), an aryl group, an aryloxy group, or a benzyloxy group, and $R^4$ represents a hydrogen atom or an alkyl group having 1 to 4 carbon atom(s) in the presence of a ruthenium-optically active phosphine complex, wherein the optically active phosphine compound constituting the ruthenium-optically active phosphine complex is an optically active substance of phosphine represented by the formula (3):

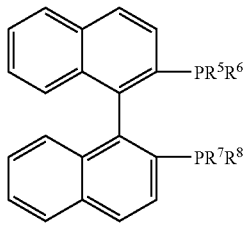

wherein each of R⁵, R⁶, R⁷, and R⁸ independently represents a phenyl group that may be substituted with a substituent selected from a group consisting of a halogen atom, a lower alkyl group, and a lower alkoxy group, a cyclopentyl group, or a cyclohexyl group, or the formula (4):

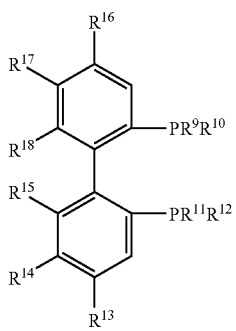

wherein each of $R^9$, $R^{10}$, $R^{11}$, and $R^{12}$ independently represents a phenyl group that may be substituted with a substituent selected from a group consisting of a halogen atom, a lower alkyl group, and a lower alkoxy group, a cyclopentyl group, or a cyclohexyl group; $R^{13}$, $R^{14}$, $^{16}$, and $^{17}$ independently represent a hydrogen atom, an alkyl group, an alkoxy group, an acyloxy group, a halogen atom, a haloalkyl group, or a dialkylamino group, and $R^{15}$ and $R^{18}$ represent an alkyl group, an alkoxy group, an acyloxy group, a halogen atom, a haloalkyl group, or a dialkylamino group; two of $R^{13}$, $R^{14}$, and $R^{15}$ may form a methylene chain that may have a substituent or a (poly)methylenedioxy group that may have a substituent and two of $R^{16}$ and $R^{17}$ and $R^{18}$ may form a methylene chain that may have a substituent or a (poly)methylenedioxy group that may have a substituent; and further, $R^{15}$ and $R^{18}$ may form a methylene chain that may have a substituent or a (poly)methylenedioxy group that may have a substituent.

2. The process according to claim 1, wherein the ruthenium-optically active phosphine complex is a complex represented by the following formula (5):

$$(Ru_aW_bX_cL_d)_eY_fZ_g \quad (5)$$

wherein L represents the optically active substance of phosphine represented by the formula (3) or (4) as in claim 1; X represents chlorine (Cl), bromine (Br), or iodine (I); and further, combinations of values represented by a, b, c, d, e, f, and g and substances represented by W, Y, and Z are any of the combinations listed in i) to vi):

i) a=2, b=0, c=4, d=2, e=1, f=1, g=0, and Y represents $N(CH_2CH_3)_3$;
ii) a=1, b=1, c=1, d=1, e=1, f=1, g=0, W represents benzene, p-cymene, or mesitylene, and Y represents chlorine (Cl), bromine (Br), or iodine (I);
iii) a=1, b=0, c=1, d=1, e=2, f=3, g=1, Y represents (μ-Cl), (μ-Br), or (μ-I), and Z represents $(CH_3)_2NH_2$ or $(CH_3CH_2)_2NH_2$;
iv) a=1, b=2, c=0, d=1, e=1, f=0, g=0, and W represents $CH_3CO_2$ or $CF_3CO_2$;
v) a=1, b=1, c=1, d=2, e=1, f=0, g=0, W represents hydrogen (H);
vi) a=3, b=0, c=5, d=3, e=1, f=1, g=0, Y represents chlorine (Cl), bromine (Br), or iodine (I).

3. The process according to claim 1, wherein the optically active phosphine compound constituting the ruthenium-optically active phosphine complex has a bidentate coordination property and at the same time an axial asymmetry.

4. The process according to claim 1, wherein the asymmetric hydrogenation is carried out in the presence of a base compound.

5. The process according to claim 2, wherein the asymmetric hydrogenation is carried out in the presence of a base compound.

6. The process according to claim 3, wherein the asymmetric hydrogenation is carried out in the presence of a base compound.

7. The process according to claim 4, wherein the base compound is selected from the group consisting of a carbonate of an alkaline metal or alkaline earth metal; an alkoxide or phenoxide of an alkaline metal; and a hydroxide of an alkaline metal or an alkaline earth metal.

8. The process according to claim 5, wherein the base compound is selected from the group consisting of a carbonate of an alkaline metal or alkaline earth metal; an alkoxide or phenoxide of an alkaline metal; and a hydroxide of an alkaline metal or an alkaline earth metal.

9. The process according to claim 6, wherein the base compound is selected from the group consisting of a carbonate of an alkaline metal or alkaline earth metal; an alkoxide or phenoxide of an alkaline metal; and a hydroxide of an alkaline metal or an alkaline earth metal.

10. The process according to claim 1, wherein the amount of the ruthenium-optically active phosphine complex is about 1/200 to 1/10000 in a molar ratio to aminophosphinylbutenoic acids represented by the formula (1).

11. The process according to claim 2, wherein the ruthenium-optically active phosphine complex is a complex selected from the group consisting of [RuCl (p-cymene)((S)-binap)]Cl, [RuCl((R)-segphos)]₂(μ-Cl)₃(Et₂NH₂), [RuCl ((R)-t-binap)]₂(μ-Cl)₃(Et₂NH₂) and [RuCl (p-cymene)((R)-binap)]Cl.

* * * * *